United States Patent [19]

Effenberger et al.

[11] Patent Number: 4,661,626
[45] Date of Patent: Apr. 28, 1987

[54] PROCESS FOR THE PRODUCTION OF 2-ISOCYANATO-2,3-DEHYDROCARBOXYLIC ACID ESTERS

[75] Inventors: Franz Effenberger, Stuttgart; Jürgen Kühlwein, Waiblingen; Karlheinz Drauz, Freigericht, all of Fed. Rep. of Germany

[73] Assignee: Degussa Aktiengesellschaft, Frankfurt am Main, Fed. Rep. of Germany

[21] Appl. No.: 837,792

[22] Filed: Mar. 10, 1986

[30] Foreign Application Priority Data

Mar. 11, 1985 [DE] Fed. Rep. of Germany ....... 3508563

[51] Int. Cl.$^4$ .......................................... C07C 122/00
[52] U.S. Cl. .................................................... 560/343
[58] Field of Search ........................................ 560/343

[56] References Cited

FOREIGN PATENT DOCUMENTS 86424 8/1983 European Pat. Off. .

OTHER PUBLICATIONS

Effenberger, Chem. Ber., vol. 117, pp. 1497–1512 (1984).

*Primary Examiner*—Alan Siegel
*Attorney, Agent, or Firm*—Cushman, Darby & Cushman

[57] ABSTRACT

There are produced 2-isocyanato-2,3-dehydrocarboxylic acid esters of the general formula:

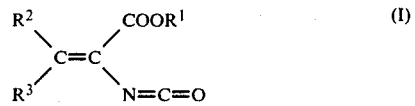

in which $R^1$ is a straight chain or branched $C_1$–$C_4$-alkyl group, a phenyl group or a benzyl group, $R^2$ is hydrogen or a methyl group and $R^3$ is hydrogen, a straight chain or branched $C_1$–$C_{16}$-alkyl group, a $C_3$–$C_8$-cycloalkyl group, a $C_1$–$C_6$-alkylmercapto group or a phenyl group by reacting a 2-azido-carboxylic acid ester of the general formula:

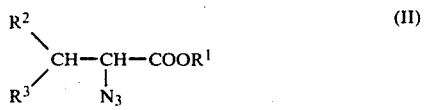

in an inert solvent at a temperature between 0° and 150° C. with phosgene or diphosgene in the presence of a perrhenate. The compounds of general formula (I) can be converted into the corresponding Z- or BOC-protected 2,3-dehydro-2-amino-carboxylic acid ester with benzyl alcohol or with tert. butyl alcohol, which esters in turn are valuable building blocks for the synthesis of dehydropeptides.

4 Claims, No Drawings

PROCESS FOR THE PRODUCTION OF 2-ISOCYANATO-2,3-DEHYDROCARBOXYLIC ACID ESTERS

BACKGROUND OF THE INVENTION

The invention is directed to a process for the production of 2-isocyanato-2,3-dehydrocarboxylic acid esters (1-alkoxycarbonyl-1-alkenyl-isocyanates) of the general formula:

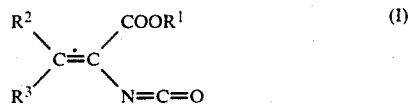

in which $R^1$ is a straight chain or branched $C_1$–$C_4$-alkyl group (e.g., methyl, ethyl, propyl, isopropyl, butyl, sec. butyl, t-butyl), a phenyl group or a benzyl group, $R^2$ is hydrogen or a methyl group, and $R^3$ is hydrogen, a straight or branched $C_1$–$C_{16}$-alkyl group (e.g., methyl, ethyl, propyl, isopropyl, butyl, t-butyl, hexyl, octyl, decyl, hexadecyl), a $C_3$–$C_8$-cycloalkyl group (e.g., cyclopropyl, cyclopentyl, cyclohexyl, cyclooctyl), a $C_1$–$C_6$-alkylmercapto group (e.g., methylmercapto, ethylmercapto, propylmercapto, isopropylmercapto, butylmercapto, hexylmercapto), or a phenyl group.

There is known from European Pat. No. 86424 a process for the production of 1-alkenyl-isocyanates which contain no additional functional groups. This process which comprises a dehydrohalogenation step to form the C=C double bond, however, is not suited for the production of compounds of general formula (I).

SUMMARY OF THE INVENTION

The invention is directed to a process of preparing 2-isocyanato-2,3-dehydrocarboxylic acid esters of formula (I) by reacting a 2-azidocarboxylic acid ester of the general formula

in which $R^1$, $R^2$, and $R^3$ are as defined above in an inert solvent at a temperature between 0° and 150° C. with phosgene or diphosgene (trichloromethyl chloroformate) in the presence of a perrhenate.

The compounds of general formula (I) have not been described previously. They can be changed in a simple reaction with benzyl alcohol or with tert. butyl alcohol into the corresponding Z- or BOC-protected 2,3-dehydro-2-amino-carboxylic acid esters, which in turn are valuable building blocks for the synthesis of dehydropeptides.

Through the process of the invention, the 2-isocyanato-2,3-dehydrocarboxylic acid esters of general formula (I) can be readily produced in a one-step process in acceptable yields.

The 2-azido-carboxylic acid esters of general formula (II) serving as starting materials can be produced according to the process described by Effenberger, Chem. Ber. Vol. 117, pages 1497–1512 (1984) by reaction of the corresponding 2-chloro- or 2-bromo-carboxylic acid esters with an aqueous sodium azide solution in the presence of a phase transfer catalyst. As example, there can be mentioned the esters of 2-azido-propionic acid, -butyric acid, 3-methylbutyric acid, -3-phenylpropionic acid, -valeric acid, -4-methylpentanoic acid, -3-cyclopropylpropionic acid, 3-cyclopentylpropionic acid, -3-cyclohexylpropionic acid, -hexanoic acid, -heptanoic acid, -octanoic acid, -nonanoic acid, -decanoic acid, -undecanoic acid, -dodecanoic acid, -tridecanoic acid, -tetradecanoic acid, -pentadecanoic acid, -hexadecanoic acid, -heptadecanoic acid, -octadecanoic acid, -nonadecanoic acid or -3-methylmercaptopropionic acid.

Suitable inert solvents for carrying out the process of the invention, for example, are carboxylic acid alkyl esters such as ethyl acetate, n-propyl acetate, isopropyl acetate, n-butyl acetate, or ethyl propionate; ethers such as dimethoxyethane, dioxane or tetrahydrofuran; furthermore, cyclohexane, toluene, or chlorobenzene.

Preferably, the process of the invention is carried out at a temperature between 20° and 100° C.

As catalysts there are suited perrhenates, especially sodium or potassium perrhenate or quaternary ammonium perrhenates such as tetraethyl ammonium perrhenate, tetrabutyl ammonium perrhenate, triethylbenzyl ammonium perrhenate or tricaprylmethyl ammonium perrheante. They are used suitably in an amount between 0.005 and 10 mole percent, preferably between 0.1 and 3 mole percent, based on the total of 2-azido-carboxylic acid of general formula (II) employed.

The phosgene can be employed as such or as diphosgene, since the latter decomposes into phosgene at elevated temperature:

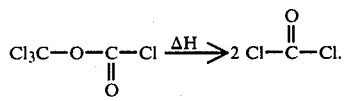

The phosgene is suitably used in an amount of at least 1 mole, the diphosgene in an amount of at least 0.5 mole, preferably between 0.51 and 1.5 moles, in each case per mole of 2-azido-carboxylic acid ester of general formula (II) employed. The molar amounts of phosgene or diphosgene to be inserted otherwise is not critical.

In using phosgene as such, this can either be led through the reaction mixture in excess in gaseous form or it can be dosed in a condensed form.

On occasion, it can be suitable before the beginning of the addition of the phosgene or diphosgene to the reaction mixture to lead dry gaseous hydrogen chloride into the solvent. The amount of hydrogen chloride likewise is not critical. It can reach up to the saturation concentration in the particular solvent.

The process of the invention, for example, can be carried out in such manner that the perrhenate and diphosgene are present in solution, in a given case additional dry hydrogen chloride is led in, and then there is dosed in the 2-azido-carboxylic acid ester of general formula II, dissolved in the same volume of the solvent used, within ten minutes to several hours at the chosen reaction temperature. It is stirred in each case up until the end of the development of nitrogen at the reaction temperature chosen.

The process can also be carried out by having the 2-azido-carboxylic acid ester of general formula (II) present together with the perrhenate in solution, in a given case additionally leading in dry hydrogen chloride, and then dosing in the condensed phosgene or diphosgene or leading in gaseous phosgene.

After the end of the development of nitrogen, the excess phosgene is then blown out of the reaction mixture with nitrogen and the reaction mixture freed of solid components by filtration. The solvent is distilled off under reduced pressure and with exclusion of moisture and the residue remaining is purified by distillation in high vacuum.

The process can comprise, consist essentially of, or consist of the stated steps with the recited materials.

Unless otherwise indicated, all parts and percentages are by weight.

The invention is further explained in the following examples.

EXAMPLE 1

27.3 mg (0.1 mmole) of sodium perrhenate and 1.04 grams (5.25 mmoles) of diphosgene were present at 80° C. in 1 ml of ethyl acetate saturated with hydrogen chloride. Then there were added within 20 minutes with vigorous stirring 1.71 grams (10 mmoles) of 2-azidohexanoic acid methyl ester dissolved in 5 ml of ethyl acetate. The reaction was ended after 1 hour uniform development of gas. The reaction mixture was then filtered with suction over a vacuum frit and the ethyl acetate distilled off under reduced pressure. The crude product thus obtained was distilled in a high vacuum (0.0013 mbar) at 50° to 55° C. apparatus temperature in a bulbed tube. There resulted 1.35 grams (79.8% of theory) of analytically pure 2-isocyanato-2-hexenoic acid methyl ester as a colorless, readily mobile liquid:

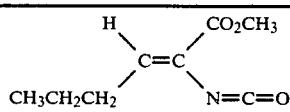

| $C_8H_{11}NO_3$ (169.18) | | | |
|---|---|---|---|
| | % C | % H | % N |
| Calculated: | 56.80 | 6.55 | 8.28 |
| Found: | 56.62 | 6.52 | 8.38 |

$^1$H-NMR (CDCl$_3$): δ=6.39 (t, 1H), CH$_2$—CH=; 3.85 (s, 3H) OCH$_3$; 2.28 (q, 2H) —CH$_2$—CH=; 1.81–1.14 (m, 2H) CH$_3$—CH$_2$—CH$_2$; 0.95 ppm (t, 3H) CH$_3$—CH$_2$, IR $_{NCO}$=2260 cm$^{-1}$, $_{CO}$=1725 cm$^{-1}$, 1655 cm$^{-1}$.

EXAMPLE 2

27.3 mg (0.1 mmole) of sodium perrhenate and 1.04 grams (5.25 mmoles) of diphosgene were present at 80° C. in 1 ml of ethyl acetate saturated with hydrogen chloride. Then there were added within 20 minutes with vigorous stirring 2.05 grams (10 mmoles) of 2-azido-3-phenylpropionic acid methyl ester dissolved in 5 ml of methyl acetate. After reaction for 1 hour at 80° C., the mixture was worked up analogous to Example 1. The crude produce was distilled in a high vacuum (0.0013 mbar) at 90° to 110° C. apparatus temperature in a bulbed tube. There resulted 1.08 grams (53.2% of theory) of analytically pure 2-isocyanato-3-phenyl-propenoic acid methyl ester.

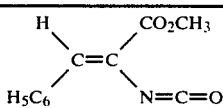

| $C_{11}H_9NO_3$ (203.197) | | | |
|---|---|---|---|
| | % C | % H | % N |
| Calculated: | 65.02 | 4.46 | 6.89 |
| Found: | 64.81 | 4.39 | 6.71 |

Melting pont: 39° to 40° C.

$^1$H-NMR (CDCl$_3$): δ=7.95–7.22 (m, 5H) aromat. —CH=C; 7.10 (s, 1H) C$_6$H$_5$—CH=; 3.9 ppm (s, 3H) OCH$_3$.

IR $_{NCO}$=2250 cm$^{-1}$, C=O=1710 cm$^{-1}$, 1643 cm$^{-1}$.

EXAMPLE 3

27.3 mg (0.1 mmole) of sodium perrhenate and 1.57 grams (10 mmoles) of 2-azido-3-methylbutanoic acid methyl ester were present in a fritted cylinder having a gas inlet tube at the bottom. Under vigorous stirring, phosgene was allowed to bubble through the reaction solution. After 2.5 hours reaction time at 80° C., the excess phosgene was blown out of the solution with nitrogen and the mixture was worked up analogous to Example 1. The crude product was distilled in a high vacuum (0.0013 mbar) at 50° to 55° C. apparatus temperature in a bulbed tube.

There resulted 1.37 grams (88.2% of theory) of analytically pure 2-isocyanato-3-methyl-2-butenoic acid methyl ester as a colorless, readily mobile liquid.

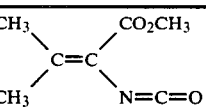

| $C_7H_9NO_3$ (155.153) | | | |
|---|---|---|---|
| | % C | % H | % N |
| Calculated: | 54.19 | 5.85 | 9.03 |
| Found: | 54.48 | 5.94 | 8.88 |

$^1$H—NMR (CDCl$_3$):
δ = 3.85 (s, 3H) OCH$_3$;

2.18 (s, 3H)H$_3$C
        \
         C=C
        /    \
              N 2.01 ppm (s, 3H)H$_3$C—⟨⟩—N.

IR $_{N=C=O}$=2250 cm$^{-1}$, $_{C=O}$=1713 cm$^{-1}$, 1630 cm$^{-1}$.

EXAMPLE 4

27.3 mg (0.1 mmole) of sodium perrhenate and 1.04 grams (5.25 mmoles) of diphosgene were present at 80° C. in 5 ml of ethyl acetate saturated with hydrogen chloride. Then there were added within 20 minutes with vigorous stirring 1.75 grams (10 mmoles) of 2-azido-3-methylmercapto-propanoic acid methyl ester dissolved in 20 ml of ethyl acetate. After reaction for 1 hour at 80° C., the mixture was worked up analogous to Example 1. The crude product was distilled in a high vacuum (0.0013 mbar) at 60° to 70° C. apparatus temperature in a bulbed tube.

There resulted 1.43 grams (82.6% of theory) of analytically pure 2-isocyanato-3-methylmercaptopropenoic acid methyl ester as a colorless liquid which solidified in the refrigeration to colorless crystals.

$$\begin{array}{c}H\\ \diagdown \\ H_3CS\end{array}C=C\begin{array}{c}CO_2CH_3\\ \diagup \\ N=C=O\end{array}$$

| $C_6H_7NO_3S$ (173.19) | | | | |
|---|---|---|---|---|
| | % C | % H | % N | % S |
| Calculated: | 41.61 | 4.07 | 8.09 | 18.51 |
| Found: | 41.86 | 4.34 | 8.20 | 18.38 |

$^1$H-NMR (CDCl$_3$): δ=7.07 (s, 1H) CH$_3$S—CH=; 3.85 (s, 3H) OCH$_3$; 2.46 ppm (s, 3H) SCH$_3$.

IR $_{NCO}$=2255 cm$^{-1}$ $_{C=O}$=1710 cm$^{-1}$, 1600 cm$^{-1}$.

EXAMPLE 5

72 mg (0.249 mmole) of potassium perrhenate and 2.6 grams (13.1 mmoles) of diphosgene were present at 80° C. in 5 ml of ethyl acetate. Then there were added within 15 minutes with vigorous stirring 4.6 grams (24.8 mmoles) of 2-azidobutanoic acid-n-butyl ester dissolved in 10 ml of ethyl acetate. The reaction was ended after 2.5 hours uniform development of gas. The reaction mixture was then filtered with suction over a vacuum frit and the ethyl acetate distilled off under reduced pressure. The crude product thus obtained was distilled in a vacuum (0.13 mbar) at 105° to 115° C. apparatus temperature in a bulbed tube.

There resulted 2.7 grams (59.4% of theory) of analytically pure 2-isocyanato-2-butenoic acid n-butyl ester.

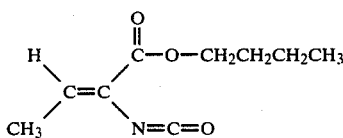

C$_9$H$_{13}$NO$_3$ (183.21)

$^1$H-NMR (CDCl$_3$/TMS): δ=6.45 (q, 1H) CH$_3$—CH=; 4.2 (t, 1H) O—CH$_2$—; 1.85 (d, 3H) CH$_3$—CH=; 0.95 (t, 3H) CH$_2$—CH$_3$; 0.65-2.0 ppm (m, 4H) —CH$_2$—CH$_2$—CH$_3$.

IR $_{NCO}$=2240 cm$^{-1}$, $_{CO}$=1715 cm$^{-1}$, 1660 cm$^{-1}$.

EXAMPLE 6

68 mg (0.249 mmole) of sodium perrhenate and 2.5 grams (12.6 mmoles) of diphosgene were present at 80° C. in 5 ml of ethyl acetate. Then there were added within 30 minutes with vigorous stirring 4.6 grams (24.8 mmoles) of 2-azidopentanoic acid isopropyl ester dissolved in 10 ml of ethyl acetate. The reaction was ended after 2 hours uniform development of gas. The reaction mixture was then filtered with suction over a vacuum frit and the ethyl acetate distilled off under reduced pressure. The crude product thus obtained was distilled in a vacuum (0.067 mbar) at 55° to 60° C. apparatus temperature in a bulbed tube.

There resulted 2.95 grams (64.9% of theory) of analytically pure 2-isocyanato-2-pentenoic acid isopropyl ester.

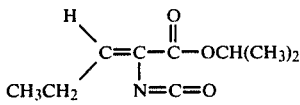

C$_9$H$_{13}$NO$_3$ (183.21)

$^1$H-NMR (CDCl$_3$/TMS): δ=6.3 (t, 1H) CH$_2$—CH=; 4.7-5.4 (m, 1H) O—CH—; 2.85-2.65 (m, 2H) —CH$_2$—CH; 1.3 (d, 6H) OCH(CH$_3$)$_2$; 1.0 ppm (t, 3H) CH$_3$—CH$_2$.

IR $_{NCO}$=2240 cm$^{-1}$, $_{CO}$=1715 cm$^{-1}$, 1650 cm$^{-1}$.

EXAMPLE 7

72 mg (0.249 mmole) of potassium perrhenate and 2.6 grams (13.1 mmoles) of diphosgene were present at 80° C. in 3 ml of ethyl acetate saturated with hydrogen chloride. Then there were added within 15 minutes with vigorous stirring 4.6 grams (24.8 mmoles) of 2-azido-hexanoic acid ethyl ester. The reaction was ended after 2 hours uniform development of gas. The reaction mixture was then filtered with suction over a vacuum frit and the ethyl acetate distilled off under reduced pressure. The crude product thus obtained was distilled in a vacuum (0.067 mbar) at 90° to 110° C. apparatus temperature in a bulbed tube.

There resulted 3.3 grams (72.6% of theory) of analytically pure 2-isocyanato-2-hexenoic acid ethyl ester.

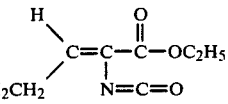

C$_9$H$_{13}$O$_3$N (183.21)

$^1$H-NMR (CDCl$_3$/TMS): δ=6.35 (t, 1H) CH$_2$—CH=; 4.25 (q, 2H) O—CH$_2$—; 2.2 (q, 2H) —CH$_2$—CH; 1.1-1.75 (m, 2H) CH$_3$—CH$_2$—; 1.25 (t, 3H) OCH$_2$—CH$_3$; 0.85 ppm (t, 3H) CH$_3$—CH$_2$.

IR $_{NCO}$=2240 cm$^{-1}$, $_{CO}$=1715 cm$^{-1}$, 1650 cm$^{-1}$.

EXAMPLE 8

72 mg (0.249 mmole) of potassium perrhenate and 2.6 grams (13.1 mmoles) of diphosgene were present at 80° C. in 5 ml of ethyl acetate. Then there were added within 20 minutes with vigorous stirring 4.95 grams (24.8 mmoles) of 2-azido-octanoic acid methyl ester dissolved in 10 ml of ethyl acetate. The reaction was ended after 2.5 hours uniform development of gas. The reaction mixture was then filtered with suction over a vacuum frit and the ethyl acetate distilled off under reduced pressure. The crude product thus obtained was distilled in a vacuum (0.11 mbar) at 105° to 115° C. apparatus temperature in a bulbed tube.

There resulted 2.8 grams (57.25% of theory) of analytically pure 2-isocyanto-2-octenoic acid methyl ester.

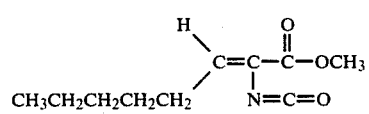

C₁₀H₁₅NO₃ (197.2)

¹H-NMR (CDCl₃/TMS): δ=6.35 (t, 1H) CH₂—CH=; 4.85 (s, 3H) O—CH₃; 2.25 (dt, 2H) —CH₂—CH=; 0.65–1.80 ppm (m, 9H) CH₃—CH₂—CH₂—CH₂—.

IR $\nu_{NCO}$=2230 cm⁻¹, $\nu_{CO}$=1725 cm⁻¹, 1650 cm⁻¹.

EXAMPLE 9

68 mg (0.249 mmole) of sodium perrhenate and 2.6 grams (13.1 mmoles) of disphosgene were present at 80° C. in 3 ml of ethyl acetate saturated with hydrogen chloride. Then there were added within 15 minutes with vigorous stirring 5.6 grams (24.6 mmoles) of 2-azido-octanoic acid isopropyl ester dissolved in 10 ml of ethyl acetate. The reaction was ended after 2 hours uniform development of gas. The reaction mixture was then filtered with suction over a vacuum frit and the ethyl acetate distilled off under reduced pressure. The crude product thus obtained was distilled in a vacuum (0.067 mbar) at 130° to 150° C. apparatus temperature in a bulbed tube.

There resulted 4.0 grams (72.2% of theory) of analytically pure 2-isocyanato-2-octenoic acid isopropyl ester.

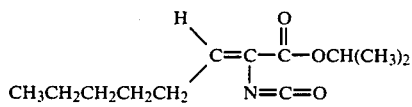

C₁₂H₁₉NO₃ (225.3)

¹H-NMR (CDCl₃/TMS): δ=6.35 (t, 1H) CH₂—CH=; 4.75–5.45 (m, 1H) O—CH; 2.25 (dt, 2H) —CH₂—CH; 1.35 (d, 6H) OCH(CH₃)₂; 0.65–1.8 (m, 9H) CH₃CH₂CH₂CH₂—.

IR $\nu_{NCO}$=2240 cm⁻¹, $\nu_{CO}$=1710 cm⁻¹, 1650 cm⁻¹.

EXAMPLE 10

72 mg (0.249 mmole) of potassium perrhenate and 2.6 grams (13.1 mmoles) of diphosgene were present at 80° C. in 5 ml of ethyl acetate. Then there were added within 15 minutes with vigorous stirring 5.25 grams (24.85 mmoles) of 2-azido-3-cyclohexylpropionic acid methyl ester dissolved in 10 ml of ethyl acetate. The reaction was ended after 2.5 hours uniform development of gas. The reaction mixture was then filtered with suction over a vacuum frit and the ethyl acetate distilled off under reduced pressure. The crude product thus obtained was distilled in a vacuum (0.09 mbar) at 140° to 150° C. apparatus temperature in a bulbed tube.

There resulted 2.7 grams (52.0% of theory) of analytically pure 2-isocyanato-3-cyclohexylpropenoic acid methyl ester.

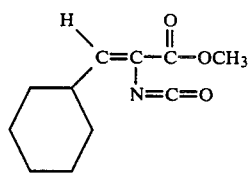

C₁₁H₁₅NO₃ (209.25)

¹H-NMR (CDCl₃/TMS): δ=6.15 (d, 1H) CH=; 3.8 (s, 3H) O—CH₃; 0.45–2.85 ppm (m, 11H)

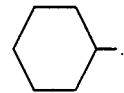

IR $\nu_{NCO}$=2230 cm⁻¹, $\nu_{CO}$=1720 cm⁻¹, 1645 cm⁻¹.

EXAMPLE 11

27.3 mg (0.1 mmole) of sodium perrhenate and 2.0 grams (10 mmoles) of diphosgene were present at 80° C. in 2 ml of ethyl acetate. then there were added within 20 minutes with vigorous stirring 1.8 grams (9.13 mmoles) of 2-azido-3-cyclopentylpropionic acid methyl ester dissolved in 2 ml of ethyl acetate. The reaction was ended after 3.5 hours uniform development of gas. The reaction mixture was then filtered with suction over a vacuum frit and the ethyl acetate distilled off under reduced pressure. The crude product thus obtained was distilled in a vacuum (0.067 mbar) in a bulbed tube.

There resulted 1.3 grams (66.6% of theory) of 2-isocyanato-3-cyclopentyl-propeonic acid methyl ester.

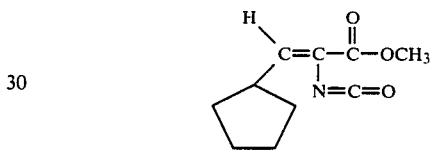

C₁₀H₁₃O₃N (195.21)

¹H-NMR (CDCl₃/TMS): δ=6.25 (d, 1H) CH=C; 3.80 (s, 3H) COOCH₃; 0.9–3.2 ppm (m, 9H)

IR $\nu_{NCO}$=2230 cm⁻¹, $\nu_{CO}$=1720 cm⁻¹, 1645 cm⁻¹.

EXAMPLE 12

68 mg (0.249 mole) of sodium perrhenate and 5.65 grams (24.4 mmoles) of 2-azido-3-cyclopentylpropionic acid isopropyl ester were present at 80° C. in 12 ml of ethyl acetate. Phosgene was led through the solution with vigorous stirring. After 4 hours reaction time at 80° C. excess phosgene was blown out of the solution with nitrogen. The reaction mixture was then filtered with suction over a vacuum frit and the ethyl acetate distilled off under reduced pressure. The crude product thus obtained was distilled in a vacuum (0.13 mbar) at 140° to 150° C. apparatus temperature in a bulbed tube.

There resulted 3.5 grams (64.2% of theory) of 2-isocyanato-3-cyclopentyl-propenoic acid isopropyl ester.

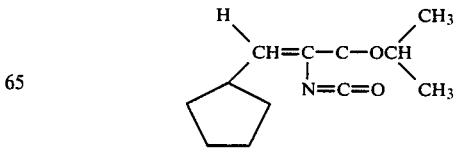

-continued

C$_{12}$H$_{17}$O$_3$N (223.27)

$^1$H-NMR (CDCl$_3$/TMS): δ=6.25 (d, 1H) CH=C; 5.75-5.45 (m, 1H) COOCH; 1.35 (d, 6H) OCH(CH$_3$)$_2$; 0.9-3.2 ppm (m, 9H)

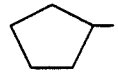

IR $_{NCO}$=2230 cm$^{-1}$, $_{CO}$=1705 cm$^{-1}$, 1645 cm$^{-1}$.

EXAMPLE 13

68 mg (0.249 mmole) of sodium perrhenate and 7.8 grams (25.04 mmoles) of 2-azido-hexadecanoic acid methyl ester were present at 80° C. in 12 ml of ethyl acetate. Phosgene was led through the solution with vigorous stirring. After 6 hours reaction time, the excess phosgene was blown out of the solution with nitrogen. The reaction mixture was then filtered with suction over a vacuum frit and the ethyl acetate distilled off under reduced pressure. The crude product thus obtained was distilled in a vacuum (0.067 mbar) in a bulbed tube.

There resulted 5.1 grams (65.8% of theory) of 2-isocyanato-2-hexadecenoic acid methyl ester.

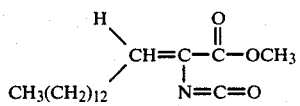

C$_{18}$H$_{31}$O$_3$N (309.45)

$^1$H-NMR (CDCl$_3$/TMS): δ=6.35 (t, 1H) CH=C; 3.85 (s, 3H) COOCH$_3$; 0.9-2.95 (m, 24H) —(CH$_2$)$_{12}$—; 0.85 ppm (t, 3H) CH$_3$—.

IR $_{NCO}$=2230 cm$^{-1}$, $_{CO}$=1710 cm$^{-1}$, 1645 cm$^{-1}$.

The entire disclosure of German priority application No. P3508563.0 is hereby incorporated by reference.

What is claimed is:

1. A process of producing a 2-isocyanato-2,3-dehydrocarboxylic acid ester of the general formula:

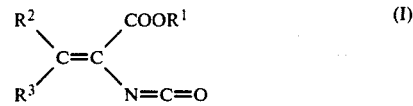

in which R$^1$ is a C$_1$-C$_4$-alkyl group, a phenyl group or a benzyl group, R$^2$ is hydrogen or a methyl group and R$^3$ is hydrogen, a C$_1$-C$_{16}$-alkyl group, a C$_3$-C$_8$-cycloalkyl group, a C$_1$-C$_6$-alkylmercapto group or a phenyl group comprising reacting a 2-azidocarboxylic acid ester of the general formula:

in an inert solvent at a temperature between 0° and 150° C. with phosgene or diphosgene in the presence of a perrhenate.

2. A process according to claim 1 wherein the perrhenate is sodium or potassium perrhenate.

3. A process according to claim 2 wherein the perrhenate is used in an amount between 0.005 and 10 mole percent, based on the amount of 2-azidocarboxylic acid ester of formula (II).

4. A process according to claim 1 wherein the perrhenate is used in an amount between 0.005 and 10 mole percent, based on the amount of 2-azidocarboxylic acid ester of formula (II).

* * * * *